United States Patent [19]

Molina

[11] 3,978,398

[45] Aug. 31, 1976

[54] METHOD FOR NONDESTRUCTIVE MAGNETIC INSPECTION OF AN OBJECT EMPLOYING A PUTTY-LIKE MAGNETIC RECORDING MEDIUM

[75] Inventor: Orlando G. Molina, Westminster, Calif.

[73] Assignee: Rockwell International Corporation, El Segundo, Calif.

[22] Filed: Nov. 29, 1973

[21] Appl. No.: 420,327

[52] U.S. Cl. ............................ 324/37; 252/62.52
[51] Int. Cl.² ....................................... G01R 33/12
[58] Field of Search ............ 324/37, 38; 252/62.52, 252/62.53, 62.54

[56] References Cited
UNITED STATES PATENTS

| | | | |
|---|---|---|---|
| 2,764,733 | 9/1956 | De Forest | 324/38 |
| 3,013,206 | 12/1961 | Youngquist et al. | 324/38 |

FOREIGN PATENTS OR APPLICATIONS

| | | | |
|---|---|---|---|
| 497,095 | 12/1938 | United Kingdom | 324/38 |
| 1,237,864 | 6/1971 | United Kingdom | 324/38 |

OTHER PUBLICATIONS

Suchow, L., New Method for Making Magnetic Fields Visible, Jour. of Appl. Physics, Feb. 1958, pp. 223-224.

Primary Examiner—Robert J. Corcoran
Attorney, Agent, or Firm—Charles T. Silberberg; L. Lee Humphries

[57] ABSTRACT

A method for nondestructive magnetic particle inspection of an object or part, especially parts having complex configurations, for detection of defects and metallurgical conditions therein, by placing a novel magnetic recording medium in the form of a magnetizable preferably putty-like material on the surface of the object, magnetizing the object and such putty-like material in contact with the object, and recording on such magnetizable putty-like material, magnetic indications of such defects and metallurgical conditions, removing the so-magnetized putty-like material from the object, placing a viewing device on the area of the magnetized putty-like material previously in contact with the object, such device preferably being one containing a suspension of weakly magnetic crystals in a transparent liquid vehicle, and having a transparent portion to permit viewing such suspension, and viewing through such device the outlines and indications of the defects and metallurgical conditions in the object, produced by the reorientation of the magnetic particles of the suspension, and corresponding to the magnetic indications recorded on the magnetized putty-like material. A novel rubbery to putty-like magnetic recording medium is preferably in the form of a silicone polymer containing magnetic particles.

11 Claims, 7 Drawing Figures

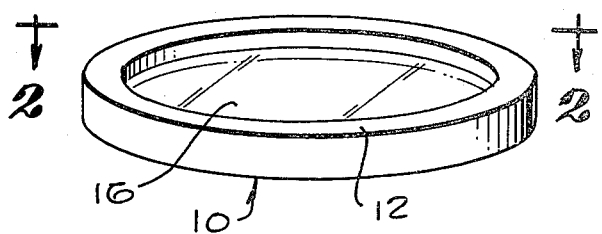
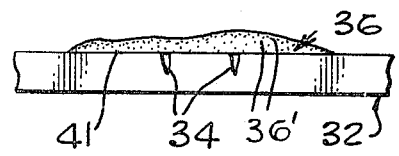
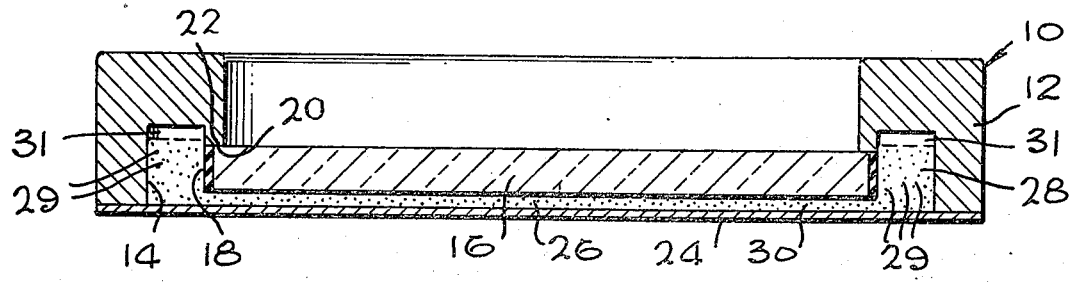
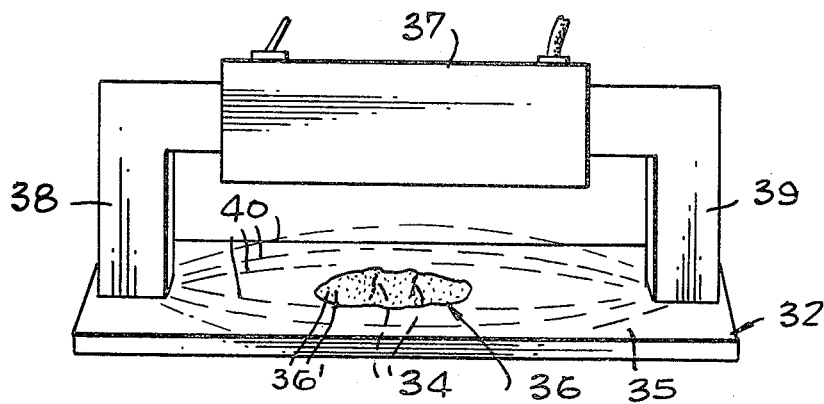
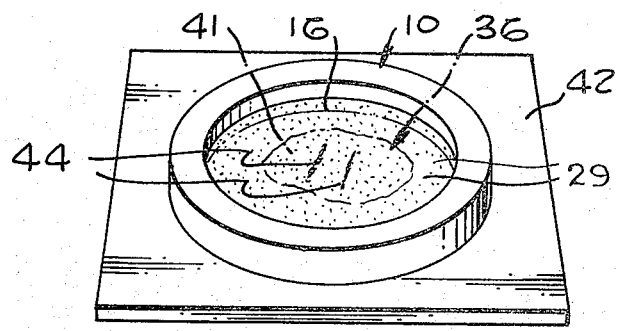
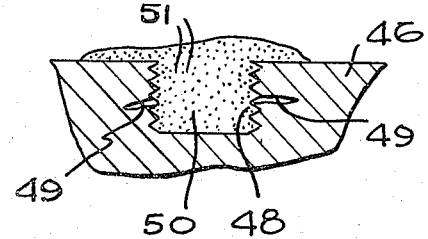

METHOD FOR NONDESTRUCTIVE MAGNETIC INSPECTION OF AN OBJECT EMPLOYING A PUTTY-LIKE MAGNETIC RECORDING MEDIUM

BACKGROUND OF THE INVENTION

This invention relates to nondestructive testing of bodies or objects by magnetic particle inspection procedure, for detection of defects and metallurgical conditions, particularly in the surface of the body, and is particularly concerned with a simple method for facile and rapid magnetic particle inspection of bodies by employing a viewing device, perferably containing weakly magnetic crystals, in conjunction with a novel magnetic recording medium of a type having properties permitting it to conform to complex surface configurations of an object, and wherein magnetic indications of defects, discontinuities and varying metallurgical conditions in the object are first recorded on such recording medium, said viewing device permitting visual observation with clarity and sharpness, of such magnetically recorded magnetic indications.

Conventional magnetic particle inspection methods for nondestructive testing of bodies generally employ solutions or powders of magnetic material such as ferromagnetic oxides, which are applied to the surface of the object and build up over cracks or defects contained in bodies of magnetic materials such as steel. In these methods the magnetic particles generally are directly deposited over the surface of the objects or parts, contaminating them. Such magnetic particles are used up in the process and they are generally not recoverable since they attach or adhere to the magnetized surface of the parts being inspected. Thus, the magnetic particles in these methods contaminate the surface of the objects being inspected. Further in these conventional methods for nondestructive flaw and crack detection, the magnetic flux applied to the object must be induced at right angles to the suspected cracks and defects for satisfactory results.

An improved method for magnetic inspection of parts is disclosed and claimed in my copending U.S. application Ser. No. 360,988 filed May 16, 1973 now U.S. Pat. No. 3,855,526. According to the latter application, a contrasting, e.g. white, background coating is applied over the surface of the object or part to be inspected, a field of magnetic flux lines is established relative to the object, and magnetic particles, preferably suspended in a suitable liquid medium, are applied over the coating, the field of magnetic flux lines causing the magnetic particles to agglomerate on the coating over the surface defects and discontinuities, and the body is inspected to reveal the defects and discontinuities as defined by the magnetic particle indications produced by the agglomerated magnetic particles.

Although the above procedure of my copending application is effective and advantageous, there is disclosed in my copending application Ser. No. 420,326, filed Nov. 29, 1973, novel magnetic inspection procedure employing a magnetic recording medium such as magnetic tape for recording magnetic indications of defects and discontinuities in the object, in conjunction with a relatively simple viewing device for viewing the outline of such defects and discontinuities corresponding to the magnetic indications thereof in such recording medium. Such procedure permits effective and rapid detection of surface cracks, flaws, discontinuities and varying metallurgical conditions, with high sensitivity, without at all contacting or contaminating the part surface with magnetic particles.

However, although the use of a magnetic recording medium such as magnetic tape in the procedure of my above copending application permits magnetic inspection of objects or parts having an irregular shape, in many instances it is necessary to inspect more complex configurations including holes, threaded areas, and sharp curvatures in objects. This is difficult to accomplish employing magnetic tape as the recording medium according to the procedure of my above copending application.

It is accordingly a particular object of the present invention to provide a novel magnetic inspection procedure employing a viewing device of the type disclosed in my above copending application Ser. No. 420,326, but including means for initially recording magnetic indications of defects and discontinuities and metallurgical conditions in a part, in the form of a magnetizable material which when applied to a part having complex configurations such as, for example, highly irregular surfaces, large cracks, holes, threaded areas and sharp curves, readily conforms to the shape of such configuration, and then viewing such recorded magnetic information in such viewing device applied to such magnetic medium, to obtain visual indications of such previously recorded indications of the surface cracks, flaws and discontinuities, and metallurgical conditions in the object or part, with a sharpness and clarity equal to that obtained when a magnetic tape is employed, in accordance with the method of my above last-mentioned copending application. Another object is the provision of a novel magnetic recording medium for use in the above method.

DESCRIPTION OF THE INVENTION

Applicant has now discovered, according to the present invention, that the cracks, discontinuities, and varying metallurgical conditions within a part or body can be readily detected by magnetic inspection technique, employing conventional magnetizing means, such as an electromagnet, and utilizing a novel magnetic recording medium comprised of a magnetizable or magnetic rubbery to putty-like material for initially recording magnetic indications of such cracks, discontinuities and varying metallurgical conditions in the magnetized body, and then viewing such recorded information on the magnetic, preferably putty-like, material by means of a viewing device, which is visually responsive to the magnetic indications recorded on such magnetic putty-like material. The viewing device employed preferably is of a type enclosing a suspension of weakly magnetic crystals in a transparent liquid vehicle and containing a transparent portion to permit viewing of the suspension, and described in my above copending application, the suspended magnetic crystals in such viewing device reorienting to form magnetic crystals indications corresponding to those recorded in the magnet putty-like recording medium, and providing sharp indications of the cracks, discontinuities and other metallurgical conditions of the part.

Such viewing devices are simple in construction, a form of such device also being disclosed in U.S. Pat. No. 3,013,206. However, as disclosed in such patent, the viewing device thereof was designed only for visual observation of magnetic signals, particularly television signals, recorded on tape and sheet, an application which is entirely unrelated to nondestructive magnetic particles testing of bodies for defects and discontinuities therein.

Thus, according to the present invention there is provided a method for nondestructive magnetic inspection of an object, for detection of defects and discontinuities, and metallurgical conditions therein, such object being composed of a magnetic material, which comprises placing a magnetic or magnetizable rubbery to putty-like material, e.g. comprised of a silicone polymer, as recording medium, on a surface of the object, establishing a field of magnetic flux lines relative to the object and the magnetic, preferably putty-like, recording medium thereon, recording on such magnetic recording medium magnetic indications or signals of the configurations of such defects and discontinuities, and metallurgical conditions in the object, preferably removing the rubbery to putty-like recording medium from the object, placing on such recording medium a viewing device for observation of the magnetic indications recorded on the rubbery to putty-like recording medium, such device preferably comprising means enclosing a suspension of weakly magnetic crystals in a transparent liquid vehicle and a transparent portion to permit viewing of such suspension, causing the weakly magnetic crystals in the suspension to reorient so as to reproduce the magnetic indications from the magnetic rubbery to putty-like recording medium, and viewing in the device the suspension of reoriented magnetic crystals, to reveal the defects and discontinuities and metallurgical conditions as defined by the reoriented crystals indications.

The term "rubbery to putty-like" as employed in the specification and claims is intended to denote materials varying from a relatively hard rubbery consistency to a highly pliable elastic consistency, specific examples of which are set forth hereinafter. However, since the putty-like materials are preferred for purposes of the invention, the invention will be described below chiefly in terms of such materials.

Preferably, in carrying out the above method, the magnetic putty-like material, having magnetic or ferromagnetic particles distributed therein, is pressed against the surface of an object to be inspected, such putty-like material being of a consistency which when relatively lightly pressed by hand conforms closely to smooth, straight or curved surfaces and to irregular or complex configurations in the object surface, including, for example, sharp surfaces or changes in surface configuration, holes, large cracks, and the like. After the object or part with the magnetic putty-like recording medium thus pressed into contact with the object, is magnetized by subjection thereof to a field of magnetic flux lines, the magnetized putty-like recording medium is removed from the part and the above-noted viewing device is pressed by relatively light pressure against the area of such putty-like recording medium which was previously pressed against the object, to thereby view the outlines and magnetic indications of the defects, discontinuities and varying metallurgical conditions in the area of the part to which the magnetic putty-like recording medium was applied.

According to the method of the present invention, the same advantages are obtained as are achieved in my above last-mentioned copending application. Thus, in the method of the present invention, the magnetic particles or crystals of neither the magnetic recording medium nor of the viewing device contaminate the surface of the object being inspected. Also, as contrasted to general prior art methods, in the present method the field of magnetic flux need not be directed at right angles to the defects or discontinuities sought to be detected. Moreover, the method of the present invention can be employed to detect flaws, defects and discontinuities on the part surface of highly irregular and complex configurations such as holes and threaded areas.

The magnetic particles or magnetic oxides incorporated in the rubbery to putty-like matrix material have high magnetic retentivity or memory, that is retain magnetism, and thus do not require migration and agglomeration when subjected to a magnetic field to form magnetic indications. After the part with the recording medium comprised of the rubbery to putty-like matrix material containing the magnetic particles, positioned on a surface of the part, has been subjected to a magnetic field, the magnetic particles or magnetic oxides in such matrix material, particularly adjacent that surface thereof in contact with the surface of the part, become magnetically sensitized. The thus sensitized magnetic particles or magnetic oxides in the rubbery to putty-like matrix material retain or "memorize" the magnetic signals produced in the part, and after removal of the recording medium comprised of such matrix material from the part surface, such recording medium can be placed flat to be "read", that is viewed by the viewing device. The invisible magnetic signals formed in such recording medium become visible with the aid of the above-noted viewing device containing the suspension of weakly magnetic crystals.

The method of the present invention employing a magnetic rubbery to putty-like material as recording medium has additional advantages. These include the ability to record indications of defects and discontinuities in an object which can be made visible at a later time or stored indefinitely to provide a permanent recording of the magnetic indications of such defects, discontinuities and metallurgical detail. In addition, such recording media, e.g. magnetic putty-like silicone polymer material, on which magnetic indications of the structural conditions of a part were previously made, can be demagnetized to erase the recorded indications and such magnetic putty-like material used over and over again with good reproducibility. It was particularly unexpected to find that use of such rubbery to putty-like magnetizable material as magnetic recording medium in the process of the present invention resulted in visual observation through the viewing device of cracks, discontinuities and metallurgical details, including heat-affected zones of the part, with sharpness and excellent resolution, equal to the results obtained employing the process of my above last-mentioned copending application.

For purposes of greater clarity, the process of the present invention is described in greater detail below, taken in connection with the accompanying drawings wherein:

FIG. 1 is a perspective view of an exemplary viewing device employed in the invention procedure;

FIG. 2 is a diametric section of the device of FIG. 1, taken on line 2—2 of FIG. 1;

FIG. 3 illustrates a part or object to be inspected and a magnetic putty-like material placed on a surface area of the object, and the establishment of a field of magnetic flux lines around the object to be inspected and the magnetic putty-like material thereon;

FIG. 4 is a sectional detail of FIG. 3, illustrating more clearly the positioning of the putty-like material over the cracks in the surface of the part;

FIG. 5 is a cross section of the magnetized putty-like material following its removal from the object surface, in the inverted position of the putty-like recording medium;

FIG. 6 illustrates placement of the viewing device of FIGS. 1 and 2 against the upper surface of the magnetized putty-like material shown in FIG. 5, for detection of cracks, discontinuities and other metallurgical conditions of the part; and FIG. 7 illustrates application of the invention process for magnetic inspection of a threaded area of an object.

It will be understood that the showings in the drawings are exaggerated for greater clarity.

Referring to FIGS. 1 and 2 of the drawing, numeral 10 illustrates a typical form of viewing device which can be employed in the invention process, and which basically is comprised of a vessel or container, which encloses a transparent liquid suspension of weakly magnetic crystals and having a transparent portion for viewing the enclosed weakly magnetic crystal suspension. It will accordingly be understood that the viewing device can be constructed in any suitable or desired manner, embodying the above-noted essential features.

The typical illustrative viewing device 10 shown in the drawing comprises a circular ring-shaped non-ferro-magnetic hollow container or vessel 12, having a hollow annular space 14 adjacent the bottom portion of the container 12. The container or ring 12 can be composed of any suitable non-ferromagnetic material such as metals, for example, brass or aluminum, or plastic, and which can be opaque or transparent, e.g. clear transparent plastic, and the like. A clear glass viewing window 16 surrounded by a resilient or elastomeric sealing member 18 is positioned across the central lower portion of the ring and is attached along its upper peripheral edge portion 20 to an adjacent horizontal shoulder 22 of the wall forming the annular portion 14, by any suitable means such as cementing. The viewing window 16, if desired, can be formed of other transparent materials such as transparent plastic, e.g, polymethacrylate or polystyrene.

A non-ferromagnetic circular metal shim 24 is attached in suitable manner to the bottom of the container or ring 12, enclosing the annular hollow portion 14 of the container 12. The thickness of the viewing window 12 is such that there is provided a broad shallow cavity 26, e.g. of about 0.010 to about 0.020 inch in depth, between the lower surface of the window 16 and the shim 24. Such shallow cavity 26 is in communication with the annular hollow portion 14 within the vessel or container 12.

Although the specific viewing device 10 described above is shown as essentially circular in shape, it will be understood that the container or housing 12 of the device can be of any other desired shape.

The transparent liquid vehicle suspension of weakly magnetic crystals is introduced in suitable manner into the annular hollow portion 14 of the container 12, forming a reservoir 28 of liquid suspension of ferromagnetic particles 29, from which the suspension of magnetic crystals passes into the interconnected broad shallow cavity 26, forming a shallow layer of transparent liquid-magnetic crystal inspection suspension at 30.

For use in the device, there can be employed a water or aqueous suspension of weakly magnetic crystals in the form of flat alpha-$Fe_2O_3$ crystals, e.g. in a concentration of about 2% by weight. The concentration of such magnetic crystals can range from about 1% to about 10%, by weight. Such aqueous suspension optionally can also include a small amount of a detergent, e.g. triethanol amine lauryl sulfate, as a wetting and antistatic agent. Although water is a preferred transparent liquid suspending medium, it will be understood that any other suitable transparent medium can be employed for suspending the weakly magnetic crystals, for example, organic solvents having a high flash point such as hydrocarbons, e.g. kerosene. The weakly magnetic crystals, such as those described above, orient when suspended in liquid in a magnetic field. The individual magnetic crystals essentially do not migrate, but simply shift position or reorient when subjected to a magnetic field. Because the liquid vehicle of the suspension is transparent and the cavity 26 containing the liquid suspension 30 is shallow, upon subjecting the suspension to a magnetic field, the reoriented crystals are clearly visible through the transparent window 16 due to presentation of varying degrees of reflectivity of such reoriented crystals to incident light. Window 16 is of sufficient thickness for strength, clarity and durability, so that the oriented magnetic crystals are clearly visible.

Although it is preferred to employ weakly magnetic crystals suspended in a transparent liquid medium, due to the almost instantaneous and rapid reorientation of such crystals when placed in a magnetic field, there can be employed alternatively strongly ferromagnetic particles such as a transparent liquid suspension of flat gamma-$Fe_2O_3$ crystals, which do not orient but rather migrate when subjected to a magnetic field to visibly outline the configuration produced by the migration of such crystals. However, because the speed at which the migration of the gamma-$Fe_2O_3$ crystal suspension reproduces the magnetized configurations of flaws and discontinuities and metallurgical conditions from the magnetic recording medium according to the present invention is slow compared to the speed of action or orientation of the alpha-$Fe_2O_3$ crystal suspension, the latter type of suspension is preferred.

The transparent liquid suspension of the weakly magnetic crystals in the shallow cavity 26 and in the annular reservoir or hollow portion 14 can be shaken from time to time, as desired, to maintain a uniform suspension and to prevent the magnetic crystals from settling out. For this purpose, the annular space 14 can be partly filled with the suspension of magnetic crystals so as to leave an air space as indicated at 31 above the reservoir 28 of suspension, so as to facilitate shaking to maintain the magnetic crystals in substantially uniform suspension and allow for expansion of the solution.

For a further detailed description of the transparent liquid suspension of magnetic crystals employed in the viewing device 10, reference is made to above U.S. Pat. No. 3,013,206.

Referring now to FIGS. 3 to 6 of the drawing, according to the process of the present invention, a part or object 32, which is composed of magnetic material, such as PH 15-7 Mo steel, a stainless steel which is poorly magnetic steel, 4130 steel, a higher magnetic steel, and the like, and having suspected defects or discontinuities therein, as illustrated at 34, is to be inspected. A magnetic recording medium in the form of a mass of putty-like material 36 containing magnetic particles, indicated at 36', is placed over the surface area of the part 32 containing such defects, and brought into close engagement with the surface of the part to prevent air gaps, as seen in FIGS. 3 and 4, by gently pressing with the fingers.

The magnetizable putty-like material, indicated at 36, functioning as magnetic recording medium, can be formed from any material which generally has the consistency of putty, that is, the material is highly pliable and moldable, but is preferably essentially non-sticky, so that it can be applied to a part surface and pressed by light pressure against the surface to fill any gaps between the putty-like material and the surface of the part, by a light pressure of the fingers, and maintained by light adhesion to the part surface, but can be easily removed from the part surface with a minimum effort, as by light peeling. Alternatively, although not preferred, putty-like materials which are sticky or tacky, and which have relatively high adhesion can be used, provided a release agent such as a Teflon (polytetrafluoroethylene), silicone or oil-like release agent, is first sprayed on the part to be inspected, to facilitate removal of such materials from the part. Thus, the putty-like matrix material of the recording medium employed herein can be made to conform readily to any highly irregular or even sharply curved surfaces, and to fill any holes in the surface area or configuration of the object. Such putty-like materials generally also display elastic properties or characteristics. Further, the material employed for this purpose retains these putty-like characteristics over long periods of time without drying out or losing these characteristics.

A particularly preferred putty-like material for this purpose are the silicone polymers. A specific material of this type which has been found especially effective is the material marketed as "Silly Putty", which is understood to be a physical mixture of a silicone oil, which is a dimethyl polysiloxane of high viscosity of the order of about 100,000 cs (centistokes), and finely divided boric acid powder. Filler materials or extenders may also be present, such as pigments, e.g. titanium dioxide, Teflon (polytetrafluoroethylene), and the like. Other silicone polymers which can be employed to produce the above-noted putty-like matrix material include, for example, methyl phenyl polysiloxanes.

As alternative putty-like materials which can be employed there can be utilized urethane polymers, particularly a polyether polyurethane. Another suitable exemplary putty-like material can be formed from carboxyl-terminated polybutadiene. Natural rubber and certain synthetic rubbers of the neoprene type can also be employed, for example certain neoprene rubbers containing cyano groups, but these materials tend to have a harder rubbery consistency.

Still another type of alternative pliable, cohesive putty-like material which can be employed as matrix material for the magnetic particles is the plastic composition formed from certain resins or gums such as guar gum. A representative plastic composition utilizing such gum is comprised of guar gum, an alkali metal borate such as borax, and boric acid, and which can also contain fillers such as Teflon, e.g. as described in U.S. Pat. No. 3,384,498, a specific composition of this type consisting of 90 parts guar gum, 5 parts boric acid, 1 part borax and 4 parts of filler such as particulate Teflon, by weight.

Magnetic particles of a type generally employed in conventional magnetic tape utilized for audio or video recording, and of high magnetic retentivity can be incorporated in the putty-like matrix to produce the magnetizable or magnetic putty-like recording medium employed in the process of the present invention. These magnetic particles can be magnetic oxides or ferromagnetic particles of a fine size, such as 325 mesh or smaller. The ferromagnetic particles, e.g. in the form of a powder, are incorporated in the putty-like matrix and evenly distributed therein so as to confer magnetic properties on the resulting putty-like matrix, and hence such resulting putty-like matrix containing the magnetic particles is magnetizable and responsive to variations in an applied magnetic field.

The magnetic particles, e.g. "3M Magnetic Powder" marketed by Minnesota Mining & Mfg. Co. can be incorporated into the putty-like material by forming a suitable suspension of the magnetic particles in an organic solvent such as methyl ethyl ketone, and mixing such suspension with the putty-like material. Alternatively the putty-like material can be mixed or slurried with a solvent such as methyl ethyl ketone and a suitable amount of magnetic particles incorporated into and mixed with such slurry. Following addition of the magnetic particles to the putty-like material by either of the methods described above, the solvent is permitted to evaporate, leaving the dried putty-like material with the magnetic particles evenly distributed therein.

The proportion of magnetic particles incorporated into the rubbery to putty-like matrix material can vary to obtain an effective magnetic recording medium for purposes of the invention. Generally, there can be employed about 5 to about 60% of the magnetic particles, by weight of such matrix material or polymer, e.g. about 20% by weight of the particles, based on the weight of the matrix polymer material. Specific compositions of this type thus can contain, for example 5, 10, 20, 30 or 40% of such magnetic particles, based on the weight of the polymer, the putty-like matrix polymer medium comprising substantially the remainder of the magnetic composition. Thus, a preferred effective magnetic recording medium according to the invention, and employed in the procedure presently described consists of a putty-like matrix material composed of the above-described "Silly Putty", containing dimethyl polysiloxane of about 100,000 cs viscosity and boric acid, having the above-noted 3M Magnetic Powder distributed or dispersed substantially uniformly in the putty-like matrix, in an amount of about 20% by weight of such matrix material.

The object or part 32 having the magnetic or magnetizable putty-like recording medium 36 in contact with the surface 35 of the part 32 and disposed over the cracks and discontinuities therein as illustrated at 34, in FIGS. 3 and 4, is magnetized by placing an electromagnet 37 over the part, legs 38 and 39 of the electromagnet being placed in contact with the part surface and over the putty-like recording medium 36. It will be understood that such magnetization of the part and the recording medium, that is the magnetizable putty-like material 36, can be effected by any conventional magnetic particle inspection equipment, e.g. electromagnet, permanent magnet or magnetic printing coil. As illustrated in FIG. 3, the magnetization of the part 32 establishes a field of magnetic flux lines indicated at 40, around the part 32 and the putty-like recording medium 36, and due to variations in magnetic permeability of the part at the location of the cracks and discontinuities, as at 34, and the resulting field leakage at such cracks and discontinuities, and the resulting variation in magnetic permeability produced in the magnetizable putty-like material 36 by the magnetic field, magnetic indications or signals of the configurations of the defects and discontinuities as at 34 in part 32, are recorded in the magnetic putty-like recording medium, particularly adjacent to the surface 41 of the recording medium 36 which is in contact with the surface 35 of part 32.

Now referring to FIGS. 5 and 6, following such magnetization of the part 32 and the magnetic putty-like recording medium 36, and recording of the magnetic indications of the part defects and discontinuities as at 34 in such medium, the putty-like recording medium 36 is removed from the part and with the medium turned downside up, as seen in FIG. 5, is placed flat on a supporting surface or table indicated at 42, with the surface 41 of the putty-like recording medium, which had previously been in contact with the surface 32 of the part facing upward. The viewing device 10 is then pressed against the surface 41 of the magnetic putty-like recording medium 36, with the opaque shim 24 of the device in contact with and pressed against the putty-like material surface 41. The magnetic signals or magnetic indications recorded on the magnetic putty-like recording medium cause the weakly magnetic crystals preferably employed and suspended in the liquid within the shallow cavity 26 in the viewing device, to quickly reorient, so as to reproduce the magnetic from the recording medium. Such reorientation of the magnetic crystals in the viewing device produces a marked change in reflectivity and a corresponding sharp outline and indication, as at 44, of the discontinuities 34 in the part. Such sharp magnetic signals in indications of the cracks and discontinuities, as for example at 44, are clearly visible through the transparent viewing window 16 of the device 10. It is noted that due to the non-migrating characteristics of the magnetic particles in the rubbery to putty-like recording medium, the magnetic recording produced therein is invisible without the use of the magnetic viewer 10. A camera, such as a still, movie, or television type, can be attached to the viewing device 10 to record these magnetic indications. It is particularly significant that the images thus formed in the viewing device, revealing the cracks, discontinuities and metallurgical details, as at 44, are equally as sharp and clear as revealed in the process of my above last-mentioned copending application Ser. No. 420,326, employing, for example, a magnetic tape recording medium.

While the putty-like recording medium 36 was pressed against the viewer 10, it was attempted to distort the magnetically recorded image of the indications of the cracks and discontinuities in the putty-like recording medium 36 by smudging the putty with the finger. No change was noted in image quality. However, when the putty-like medium 36 containing the magnetic particles was elongated, the viewer 10 then showed that the magnetically recorded indications were also distorted by the deformation of the putty-like material.

After viewing the magnetic indications or images of the cracks and discontinuities in the putty-like magnetic recording medium 36, such medium was demagnetized, and the viewer no longer showed an image of the above-noted indications. The putty-like recording medium was again reused, that is, remagnetized while pressed against another part in the manner described above for inspecting the outlines and configurations of defects and discontinuities in such part, and excellent images thereof were again obtained by viewing the so-magnetized putty-like recording medium through viewer 10.

It will be understood that the viewer 10 can be moved along the surface of the putty-like recording medium 36 until the suspected cracks and discontinuities are located. While the viewer 10 is so moved along the surface of the medium 36, the viewer is constantly recording changes of magnetic permeability of the magnetic signals recorded in such medium, corresponding to the cracks and discontinuities in the part, with a movie-like effect. In other words, there can thus be provided a continuous graphic view by means of the viewing device 10 of the magnetic changes distributed throughout the putty-like recording medium, corresponding to the location of the cracks, discontinuities or changes in metallurgical construction throughout the part. If desired, the magnetic putty-like recording medium 36 with this recorded magnetic information thereon can be stored and maintained as a record.

Referring now to FIG. 7, there is shown the application of the invention principle for inspecting or viewing defects in a threaded area of a part. In FIG. 7, there is shown a part 46 having a threaded area 48 therein and containing cracks such as indicated at 49. A suitable polymer or resin in liquid form capable of curing or hardening to a rubbery consistency and containing magnetic particles is poured into the threaded area 48 and is permitted to cure or harden therein. A suitable polymer material for this purpose is a liquid silicone polymer, e.g. dimethyl polysiloxane or methyl phenyl polysiloxane, in liquid form and containing a suitable curing agent and/or catalyst. An exemplary form of polymer material for this purpose is the material marketed as RTV silicone rubber by Dow Corning, comprised of a curable dimethyl polysiloxane, and which can have a molecular weight ranging from about 6,000 to about 250,000, in which is incorporated about 5 to 10% of a curing agent such as ethyl silicate, based on the polysiloxane to be cured, and a similar small amount of a catalyst such as stannous octoate, and which may also contain a filler such as silica, talc or glass micro-balloons. A silicone polymer composition of this type can be cured at room temperature in a relatively short time, e.g. about 5 to 15 minutes, to a rubbery elastic material forming a plug 50 in the threaded area 48 with an external threaded surface matching the threaded area 48 in the part. It will be understood that other curable polymers forming a cured material having a firm rubbery consistency also can be employed, such as natural rubber or neoprene-type polymers.

There is added to the liquid polymer composition, magnetic or ferromagnetic particles as described above in suitable amount, e.g. about 5 to about 60%, by weight of such liquid polymer composition. The resulting liquid composition is mixed or stirred so as to distribute substantially uniformly therein, the magnetic particles, prior to pouring the resulting liquid polymer mixture or suspension into the holes or threaded areas, e.g. 48 of the part.

After curing the plug of magnetizable recording medium, the part containing such plug in the threaded area thereof is magnetized as described above. After suitable magnetization, as illustrated in FIG. 3 and described above, the plug of magnetic rubbery recording medium 50 containing the magnetic particles 51 is carefully removed or unscrewed from the threaded area 48, and a viewer such as 10 above is placed against the external peripheral area of the plug 50 which was disposed adjacent the threaded area 48 of the part, for visible location of the cracks or defects 49 in the threaded area 48 of the part.

Alternatively, a cast or mold can be made of such holes or interiors of parts to be inspected, as for example the threaded area 48 of part 46, and a plug of the rubbery recording material such as 50 can be made in such mold and such plug inserted or threaded into the holes such as the threaded area 48 of the part 46. After suitable magnetization, such cast or plug can be removed from the holes or threaded areas and a viewer as at 10 placed against the peripheral surfaces of the part for viewing the indications of the defects in the part adjacent such holes or threaded area. These cast rubbery plugs can be demagnetized, thus erasing the magnetic signals of the defects, and reused.

The following are examples of practice of the invention:

EXAMPLE 1

On the surface of a PH 15-7 Mo steel part containing cracks of varying size including gross cracks and microcracks, was placed a piece of "Silly Putty" having the composition noted above and containing about 20% by weight of the putty, of "3M Magnetic Powder," and the putty constituting the magnetic recording medium was spread on the part surface to cover the area containing the cracks. The putty-like recording medium was prepared by forming a suspension of the magnetic powder in methyl ethyl ketone and mixing the suspension or slurry of the magnetic particles with the "Silly Putty" in an amount such as to incorporate 20% of said particles by weight of the putty, into the putty material, following removal of the solvent. The solvent was then permitted to evaporate.

The part having the putty containing the magnetic particles, on the surface of the part was magnetized by placing an electromagnet on the part. Following such magnetization of the part and the putty containing the magnetic particles, to produce a magnetic recording on the putty, the magnetized putty was removed from the part surface and placed downside up on a table. The viewer 10 was then pressed against the surface of the magnetized putty recording which was previously in contact with the part surface, as illustrated in FIG. 6 of the drawing. Sharp images of the magnetic indications of the location and size of all of the various size cracks in the part surface were clearly visible in the suspension of weakly magnetic crystals in the viewer through the window thereof.

EXAMPLE 2

The procedure of Example 1 was substantially followed for detecting cracks in a 4130 steel part containing both large and small cracks in the surface thereof.

In the present example, however, a guar gum composition was employed as the recording medium, such guar gum composition containing about 10% by weight thereof, of about 325 mesh ferromagnetic particles distributed in the gum matrix.

After applying the guar gum containing the magnetic particles to the part surface, the part was magnetized by placing a permanent magnet over the part.

Following removal of the magnetized guar gum recording medium from the part surface, and pressing the viewer 10 against the surface of the guar gum recording medium previously in contact with the part surface, sharp clear images of the magnetic indications showing the outlines of the cracks of varying sizes in the part surface, were visible in the weakly magnetic crystals suspension contained in the viewer.

EXAMPLE 3

A magnetic steel part having cracks in the wall of a threaded area therein was inspected by first pouring into the threaded area a liquid silicone composition comprising a curable dimethyl polysiloxane containing ethyl silicate as curing agent and stannous octoate as catalyst, and a silica filler, the liquid silicone composition also having about 15% by weight thereof, of ferromagnetic powder dispersed in such composition.

The liquid silicone composition was cured at room temperature. The part containing the cured silicone plug filling the threaded area was subjected to a magnetic field by placing an electromagnet on the part. The magnetized plug of silicone was then removed from the part by unscrewing the plug from the threaded area. The magnetized plug was placed on a support surface and the viewer 10 was pressed against the threaded area of the plug, revealing in the magnetic crystals suspension of the viewer, magnetic indications corresponding to the outlines and locations of the cracks in the threaded area of the part, as initially recorded in the silicone recording medium.

EXAMPLE 4

The procedure of Example 3 was followed, except that a mold of the threaded area of a similar magnetic part was first made and the curable liquid silicone composition of Example 3 was placed in the mold and the silicone composition cured at room temperature.

The cured silicone plug was removed from the mold and inserted as by threading into the threaded area of the part.

The part was then subjected to magnetization, the magnetized silicone plug unscrewed from the threaded area of the part, and the viewer 10 pressed against the threaded wall of the plug. Observation through the window of the viewer showed magnetic indications in the weakly magnetic suspension, of the cracks in the threaded area of the part, as sharply and clearly as in Example 3.

From the foregoing, it is seen that the invention provides a unique nondestructive testing method for obtaining rapid magnetic particle inspection of an object or part, by means of a relatively simple and inexpensive viewing device comprising a transparent liquid suspension of weakly magnetic crystals, utilized in conjunction with a novel magnetic recording medium in the form of a magnetic or magnetizable rubbery to putty-like material, preferably a silicone polymer, having suitable viscosity characteristics and containing magnetic particles, without contaminating the part surface with conventional magnetic particle inspection solutions or powders, and without waste of ferromagnetic particles. The present invention procedure is particularly valuable where there are complex irregularities, sharp curvatures, holes and threaded areas in the part. When employing the magnetic recording medium noted above for initially recording the magnetic indications of defects and discontinuities in the part, because of the moldability and compliance of such putty-like recording medium, the part can have any configuration of part surface, and the putty-like recording medium can be brought into contact with any irregular surface. As previously noted, the present process has the advantage that the magnetic recording medium with the recorded information concerning the structure of the part can be stored for later viewing or reference, and can be erased and reused readily.

An additional advantage of the present invention is its application for detection of defective conditions in aircraft in the field. For this purpose, no post-cleaning and removal of primers, paints and other protective coating is necessary when employing the present method.

The present invention process is also useful in the shop where contamination of newly manufactured parts with conventional magnetic particle inspection solution is undesirable. The present method is also useful in the laboratory for recording changes in metallurgical specimens or parts being tested for fatigue cracking.

While I have described particular embodiments of my invention for the purpose of illustration within the spirit of the invention, it will be understood that the invention is not to be taken as limited except by the scope of the appended claims.

I claim:

1. A method for nondestructive magnetic inspection of an object, for detection of defects and discontinuities and metallurgical conditions therein, said object being composed of a magnetic material, which comprises placing a magnetic recording medium in the form of a magnetizable putty-like material containing magnetic particles distributed therein, on a surface of said object, establishing a field of magnetic flux lines relative to said object and said recording medium thereon, recording on said magnetic putty-like recording medium magnetic indications or signals of the configurations of said defects and discontinuities and metallurgical conditions in said object, removing said magnetized putty-like recording medium from said object, placing on said magnetized putty-like recording medium a viewing device for observation of said magnetic indications recorded on said recording medium, said device comprising means enclosing a suspension of weakly magnetic crystals which orient when suspended in liquid in a magnetic field, in a transparent liquid vehicle and a transparent portion to permit viewing said suspension, causing said weakly magnetic crystals in said suspension to reorient so as to reproduce said magnetic indications from said recording medium, and viewing in said device said suspension of reoriented magnetic crystals providing said magnetic indications of said defects and discontinuities and metallurgical conditions, said putty-like material being selected from the group of polymers and resins consisting essentially of silicone polymers, polyether polyurethanes, natural rubber, neoprene, carboxyl terminated polybutadiene and guar gum, said polymers and resins having a viscosity such that they have putty-like characteristics.

2. A method as defined in claim 1, said putty-like material containing about 5 to about 60% of fine magnetic particles, by weight of said material.

3. A method as defined in claim 1, said putty-like material being a silicone polymer.

4. A method as defined in claim 3, said silicone polymer being comprised of dimethyl polysiloxane.

5. A method as defined in claim 4, said silicone polymer having putty-like characteristics and being comprised of a mixture of silicone oil having a viscosity of about 100,000 centistokes and finely divided boric acid powder, and said magnetic particles being ferromagnetic particles, present in an amount of about 5 to about 60% by weight of said silicone polymer.

6. A method as defined in claim 1, said container being a rigid container and said transparent portion being a transparent window disposed on one side of said shallow cavity to permit visual observation of said magnetic crystal suspension in said cavity, and including an opaque member on the opposite side of said cavity from said transparent window.

7. A method as defined in claim 6, said transparent liquid vehicle being water, and said crystals being weakly magnetic alpha-$Fe_2O_3$ crystals.

8. A method as defined in claim 1, employing as said recording medium a non-sticky silicone polymer which is demagnetizable and reusable.

9. A method for nondestructive inspection of an object, for detection of defects in a threaded area of said object, said object being composed of a magnetic material, which comprises forming a liquid composition of a polymer capable of curing or hardening to a rubbery consistency, and containing magnetic particles, hardening said liquid composition to form a plug of magnetic recording medium having a rubbery consistency and containing magnetic particles distributed therein, establishing a field of magnetic flux lines relative to said object and said recording medium thereon, recording on said magnetic recording medium magnetic indications or signals of the configurations of any defects in said threaded area of said object, unscrewing said magnetized plug from said threaded area of said object, pressing against said magnetized recording medium a viewing device for observation of said magnetic indications recorded on said recording medium, said device comprising means enclosing a suspension of weakly magnetic crystals which orient when suspended in liquid in a magnetic field, in a transparent liquid vehicle and a transparent portion to permit viewing said suspension, causing said weakly magnetic crystals in said suspension to reorient so as to reproduce said magnetic indications from said recording medium, and viewing in said device said suspension of reoriented magnetic crystals providing said magnetic indications of any defects in said threaded area of the object.

10. A method as defined in claim 9, said magnetized rubbery plug being demagnetizable and reuseable.

11. A method as defined in claim 9, said plug being formed of a silicone polymer having magnetic particles distributed therein.

* * * * *